US009128061B2

United States Patent
Parusel et al.

(10) Patent No.: US 9,128,061 B2
(45) Date of Patent: Sep. 8, 2015

(54) MEASURING DEVICE AND METHOD FOR DETECTING THE HYDROCARBON CONTENT IN GASES

(75) Inventors: Franz Joseph Parusel, Langenfeld (DE); Max Penth, Lebach (DE); Bernd Penth, Lebach (DE)

(73) Assignee: Beko Technologies GMBH (DE)

( * ) Notice: Subject to any disclaimer, the term of this patent is extended or adjusted under 35 U.S.C. 154(b) by 403 days.

(21) Appl. No.: 13/202,152

(22) PCT Filed: Feb. 18, 2010
(Under 37 CFR 1.47)

(86) PCT No.: PCT/EP2010/052080
§ 371 (c)(1),
(2), (4) Date: Mar. 30, 2012

(87) PCT Pub. No.: WO2010/094750
PCT Pub. Date: Aug. 26, 2010

(65) Prior Publication Data
US 2012/0279277 A1     Nov. 8, 2012

(30) Foreign Application Priority Data

Feb. 18, 2009  (DE) .......................... 10 2009 009 404

(51) Int. Cl.
  *G01N 27/62* (2006.01)
  *G01N 27/66* (2006.01)
  *G01N 33/00* (2006.01)
(52) U.S. Cl.
  CPC ............ *G01N 27/66* (2013.01); *G01N 33/0024* (2013.01); *G01N 33/0006* (2013.01); *G01N 33/0026* (2013.01); *G01N 33/0047* (2013.01)
(58) Field of Classification Search
  USPC .............. 73/23.35, 1.06, 23.31, 31.05, 23.22, 73/23.39, 23.42
  See application file for complete search history.

(56) References Cited

U.S. PATENT DOCUMENTS

| | | | | |
|---|---|---|---|---|
| 3,558,283 A | * | 1/1971 | Freeman et al. | 436/143 |
| 3,692,492 A | * | 9/1972 | Poli et al. | 422/54 |
| 3,762,878 A | * | 10/1973 | Villalobos | 436/143 |
| 3,924,442 A | * | 12/1975 | Kerho et al. | 73/23.21 |
| 4,586,367 A | * | 5/1986 | Lewis | 73/23.33 |
| 5,297,432 A | * | 3/1994 | Traina et al. | 73/864.34 |
| 5,563,330 A | * | 10/1996 | Kimmig | 73/23.21 |
| 5,852,227 A | * | 12/1998 | Garthe | 73/23.32 |
| 6,202,408 B1 | * | 3/2001 | Lepperhoff et al. | 60/278 |
| 6,726,882 B2 | * | 4/2004 | Raisanen | 422/98 |

FOREIGN PATENT DOCUMENTS

JP    2002-323485 A    11/2002

OTHER PUBLICATIONS

International Search Report mailed Jun. 8, 2010 in International Application No. PCT/EP2010/052080 (7 pages).
Papamichail, Nikos, et al. "Monitoring of oil aerosol contaimination in pressurised air with SnO2-based thick film sensors in real life conditions", pp. 61-66, 2004.

* cited by examiner

*Primary Examiner* — Hezron E Williams
*Assistant Examiner* — Xin Zhong
(74) *Attorney, Agent, or Firm* — McCarter & English, LLP

(57) ABSTRACT

The invention relates to a measuring device for detecting the hydrocarbon fraction in gases. The measuring device is characterized in that the measuring device determines the hydrocarbon fraction in a first gas flow and a second gas flow, both the first gas flow and the second gas flow originating from the same gas source, the first gas flow being fed to the measuring device unchanged and the second gas flow being fed to the measuring device prepared.

9 Claims, 3 Drawing Sheets

MEASURING DEVICE AND METHOD FOR DETECTING THE HYDROCARBON CONTENT IN GASES

This application is the U.S. National Phase of International Application No. PCT/EP2010/052080, entitled "Measuring Device and Method for Detecting the Hydrocarbon Fraction in Gases" filed Feb. 18, 2010, designating the United States, and claiming priority to DE 10 2009 009 404.0 filed Feb. 18, 2009, the disclosures of which are hereby incorporated by reference in their entirety.

FIELD OF THE INVENTION

The present invention relates to a measuring device and a method for detecting the hydrocarbon content in gases.

BACKGROUND OF THE INVENTION

Such measurement apparatus are known with various sensor technologies and serve for detecting the contents of oil, hydrocarbons and oxidizable gases, for example in air or compressed air. Electrically heatable semiconductor oxide materials are frequently used, for instance, which, in the heated state, change their electrical resistance depending on the quantity of the hydrocarbons contained in the air.

Another method is the detection of hydrocarbons by means of elestors. To this end, the gas stream to be measured is conducted over a body of heated catalyst material in whose interior a heated coiled platinum filament is located. The hydrocarbon concentration can be detected through the change of electrical resistance of the heated and a second coiled platinum filament, which is due to the heat of combustion of the hydrocarbon content on the catalyst.

The use of flame ionization detectors is also known. In such devices, the hydrocarbons are burned in a gas stream and the change in the voltage between two electrodes in the flame is measured.

Another method is the detection of the hydrocarbon concentration by means of photoionization. In the process, the hydrocarbons are irradiated with ultraviolet light. The amount of energy of the light has to be so high in this case that electrons are forced out of the hydrocarbon. Their number can be measured by means of electrodes.

The above-mentioned methods are particularly suitable for the detection of higher concentrations in oxidizable gases; however, the detection of lower concentrations in the lower $\mu g/Nm^3$ range or the ppb range in a reliable manner is not possible.

The measured values generated by means of photoionization detectors only allow for indirect conclusions to be drawn with regard to the measured amount of substance because the measured values are also dependent on the atomic structure of the compound and vary rather considerably even given the same empirical formulas. However, provided the compound to be measured is constant, known and, if possible, also uniform, the concentration of the hydrocarbon content can be measured relatively reliably. However, the measuring accuracy is reduced as the hydrocarbon concentration decreases. In particular, the influence of the humidity content of the air rises in this case. As the hydrocarbon content decreases, the influence of air humidity becomes increasingly larger; measurements of hydrocarbon contents in the lower $mg/Nm^3$ range, and in particular in the $\mu g/Nm^3$ range, cannot be carried out with sufficient accuracy.

Different threshold values of the oil content are required for different applications of compressed air. Oil contents consist of drop-like oil aerosols and of oil vapors. Oil aerosols and oil vapors can be partially or largely eliminated from the compressed air stream by means of various methods. However, a realtime measurement of oil in compressed air is a hitherto unsolved problem.

SUMMARY OF THE INVENTION

The object of the invention lies in providing a measuring device for the detection of the content of oil, hydrocarbons and oxidizable gases in gases, which, on the one hand, measures even the lowest concentrations reliably, and on the other hand, does not have the drawbacks of the prior art. Here, the measuring device is supposed to have as simple a structure as possible and to be producible with relatively little effort. Furthermore, it is the object of the invention to provide a method for detecting the content of oil, hydrocarbon content and oxidizable gases in gases that is improved over the prior art.

The object is achieved by a generic measuring device for detecting the hydrocarbon content in a first gas stream and a second gas stream, with both the first gas stream as well as the second gas stream originating from the same gas source, the first gas stream being fed to the measuring device unchanged and the second gas stream being fed to the measuring device processed.

Furthermore, the object is achieved by a method for detecting the content of oil, hydrocarbons and oxidizable gases in a gas stream which is characterized by a source gas being divided into a first gas stream and a second gas stream, with a suitable measuring device examining both the first as well as the second gas stream, wherein the first gas stream is fed to the measuring device unchanged and the second gas stream is fed to the measuring device processed.

According to the invention, the measuring device thus, directly or via a reference gas generator, feeds the gas stream to be measured to the sensor in an alternating manner, for example by means of magnetic valves. A catalyst or oxidation catalyst, for example, can be used as a reference gas generator. The measured value is thus determined as a signal difference between the measuring gas and the generated reference gas, that is, the oxidized measuring gas.

In a particularly advantageous embodiment, the detection of the hydrocarbon contents is based on the principle of photoionization. For this purpose, the measuring device consists of two main components, a sensor unit with a sampling probe and an evaluation unit with an electronic evaluation system and a control surface (display). At the same time, the control surface can be configured as an input unit, for example by means of a touchscreen. In this case, the sensor unit is connected to the evaluation unit via a signal cable or wirelessly. Preferably, the sampling probe can be mounted centrally into a riser from above, so that it is able to extract gas centrally from the gas stream to be monitored. The sensor unit comprises defined flow resistors that provide for a constant pressure and a constant volumetric flow rate of the individual measuring gases and which are formed, for example, by a throttle with a defined bore, or from a sintered metal. They are particularly low-maintenance and simple to clean. Furthermore, an alarm function is provided which informs the user visually or acoustically in the case the pressure of the gas stream is too low or too high.

As was already indicated above, the measuring principle of the photoionization detector (PID) is based on the ionization of gas molecules by UV radiation and the detection of the ion current generated in the process. The strength of the ion current is directly proportional to the concentration of the ionized molecules. The electrical signal can thus be measured, electronically amplified and displayed on the display as a concentration of the measured substances.

It was found that the minute increase of humidity due to the oxidation in the reference gas is negligible if photoionization lamps having 10.6 eV are used during the measurement, since the influence of air humidity is the lowest with them.

According to the invention, however, it is also possible to admix a dry test gas to the reference gas stream so as to thus obtain a reference gas which corresponds to the measuring gas in its humidity content. Advantageously, it is possible to reduce the so-called drift zero line and its influence on the measurement result. Compared with other types of sensor for hydrocarbon contents, the drift zero line of a PID sensor is only small, however, it has an increased effect as the concentrations become lower. Due to the measured value being determined as a signal difference between the measuring gas and the reference gas and the two measured values drifting equally, the drift of the sensor thus has a significantly smaller influence on the measured value, in particular if an average is taken over many measurements. Given a linear drift and equal switching times, the probability of the drift being eliminated in the average value is relatively high.

According to the invention, it is further possible to reliably compensate the change of the signal strength due to aging and soiling of the measuring device. It was shown that the measuring sensitivity of the sensor fluctuates greatly over time, i.e. in particular depending on the aging of the sensor, with the signal strength also changing gradually due to the UV lamp becoming soiled. For example, the lamp window can become soiled by the substances contained in the air stream depositing on the window surface and coking them up. The measuring device according to the invention enables a calibration of the measurement sensitivity over the life of the measuring device by a calibration gas and a zero gas, in addition to the unchanged measuring gas and the reference gas, being used regularly for redetermining the signal strength provided by the sensor. Zero gas (e.g. synthetic air) does not contain any hydrocarbons or humidity, calibration gas (e.g. isobutene), however, has a defined hydrocarbon content, but also no or only an exceedingly low humidity. By means of the magnetic valves, the two auxiliary gases are alternately fed to the sensor. A data storage device provided according to the invention in the measuring device contains so-called response factors of important and known test gases and their molecular weights. From the difference between the measurement results, the measuring device, using an appropriate processor, is able to calculate a factor as a relation between measurement results and the test gas in weight per volume. This factor, which inevitably changes over time, can be stored as a calibrating factor, or is automatically stored by the measuring device and then taken as a basis for the actual measurement.

According to the invention, the calibration measurement can take place automatically at regular intervals, however, it can also be triggered at any time by the user.

It was further found that the air humidity can have a negative influence upon the signal strength. This is the case particularly if the air humidity fluctuates greatly. If, for example, air exits behind a refrigeration dryer, the fluctuations of the air humidity are significantly lower, but even they cannot be neglected given the extremely small hydrocarbon contents to be measured. For this reason, it is possible with the measuring device according to the invention to carry out a calibration measurement between the zero gas and the calibration gas in such a way that the influence of the current air humidity is eliminated. For this purpose, the auxiliary gases used for calibration are provided with the same air humidity as it is also present in the measuring gas. In contrast to known comparable measuring devices, commercially available zero gas is not exclusively used for calibration, but rather is a calibration gas used which is converted into a zero gas by being fed to a reference gas generator. In this case, the term zero gas should not be taken literally, that is, in the sense that there is no humidity present in the gas, but rather, a reference gas is available for calibration which, besides the hydrocarbon content, has the same ingredients and exactly the same air humidity as the measuring gas that is actually to be measured.

According to the invention, instead of a commercially available test gas, a mixture can be used which is formed from 90-100% reference gas and, correspondingly, 0-10% of a commercially available test gas. A diluted calibration gas is thus produced which has a humidity content which approximately corresponds to that of the measuring gas to be measured. By generating a calibration gas on-site it can be adapted in its composition to the prevailing conditions in an appropriately controlled manner by modifying parameters. It is also a decisive factor that the addition of an amount of supplied commercially available test gas into the reference gas is small and the hydrocarbon content has the same order of magnitude as the expected measurement range for the hydrocarbon content in the measuring gas.

For measuring the residual oil content in the range below Class 1 according to DIN ISO 8573-1 (i.e. <10 µg oil/Nm$^3$ gas or air), only a small amount, if possible, of the test gas is introduced into the reference gas stream in order to generate the calibration gas, so that the result with regard to the concentration is a content of <10 µg isobutene/Nm$^3$ gas or air, which corresponds to less than 3.99 ppm isobutene.

The flow volume of the various gas streams can be influenced with corresponding, optionally standardized throttles, valves or flow reducers. They are preferably replaceable and, in a particularly advantageous embodiment, controllable in order to be able, on the one hand, to adjust the flow volume to the sensor and, on the other hand, to reliably ensure the desired mixing ratios of the gas streams to be mixed.

Common oxidation catalysts can be used as reference gas generators, however, other devices or methods for providing gases with the desired properties are also conceivable. Platinized quartz wool, for example, which can be inserted into a container provided therefor without any trouble, serves as an oxidation catalyst. In a particularly advantageous version, the reference gas generator is integrated into the measuring device, whereby only the various fluid or gas feeds have to be connected on-site. Thus, the measuring device comprises all the connectors for the corresponding gas pipes and also the electrical connector, so that it can be flexibly installed on-site anywhere. In particular the division according to the invention of the measuring device into the sensor unit with the sampling probe and the evaluation unit with a control surface (display) additionally expands the possibilities for an on-site installation that is flexible with regard to space. The evaluation unit with the control surface is of a small construction and can be installed almost anywhere, preferably at an easily accessible position, whereas the slightly larger sensor unit can be disposed spatially separate from the evaluation unit at the measuring gas sampling location.

According to the invention, the measuring device has an inlet for a measuring gas, which, in accordance with the regulation regarding isokinetic sampling according to DIN/ISO 8753, is taken from a flowing gas, but not guided through a flow resistor. It is thus possible that the sensor is not exposed to any turbulences even given relatively large amounts of gas, which could lead to the measurement signal being distorted. Whether the analyses match can be checked by a comparative measurement with a measuring gas stream that was fed through a flow resistor. It is thus possible, according to the invention, to replace the isokinetic measurement in normal operation largely by a measurement with a reduced gas flow.

Preferably, the measuring device according to the invention can be used with an oil-free compressor for producing compressed air or compressed gas; however, the use of an oil-lubricated compressor is also conceivable if a corresponding catalyst is provided downstream therefrom. A bypass is preferably provided for maintenance work.

Within the context of this invention, a distinction is made between the following gas streams. The term measuring gas describes the gas to be measured, for example ambient air. Zero gas refers to a gas stream which comprises no humidity and no hydrocarbons. Reference gas is the gas stream that branches off from the measuring gas and was fed over a reference gas generator, for example an oxidation catalyst. Calibration gas refers to a gas used for the calibration of the measuring device and containing a defined amount of hydrocarbons. Test gas is a commercially available and defined gas; however, it may also be a mixed gas of, for example, zero gas and a small content of sensor-active gas.

The duration of the feed of the gas streams to the sensor can be adapted to the on-site conditions; however, an alternating feed for a duration of about 20 seconds has proved to be productive.

The invention will be explained in more detail with reference to the attached figures. In this case, the Figures merely show an advantageous embodiment; however, the invention itself is not supposed to be limited thereto under any circumstances. In the figures:

DETAILED DESCRIPTION OF EMBODIMENTS OF THE INVENTION

Figure 1:
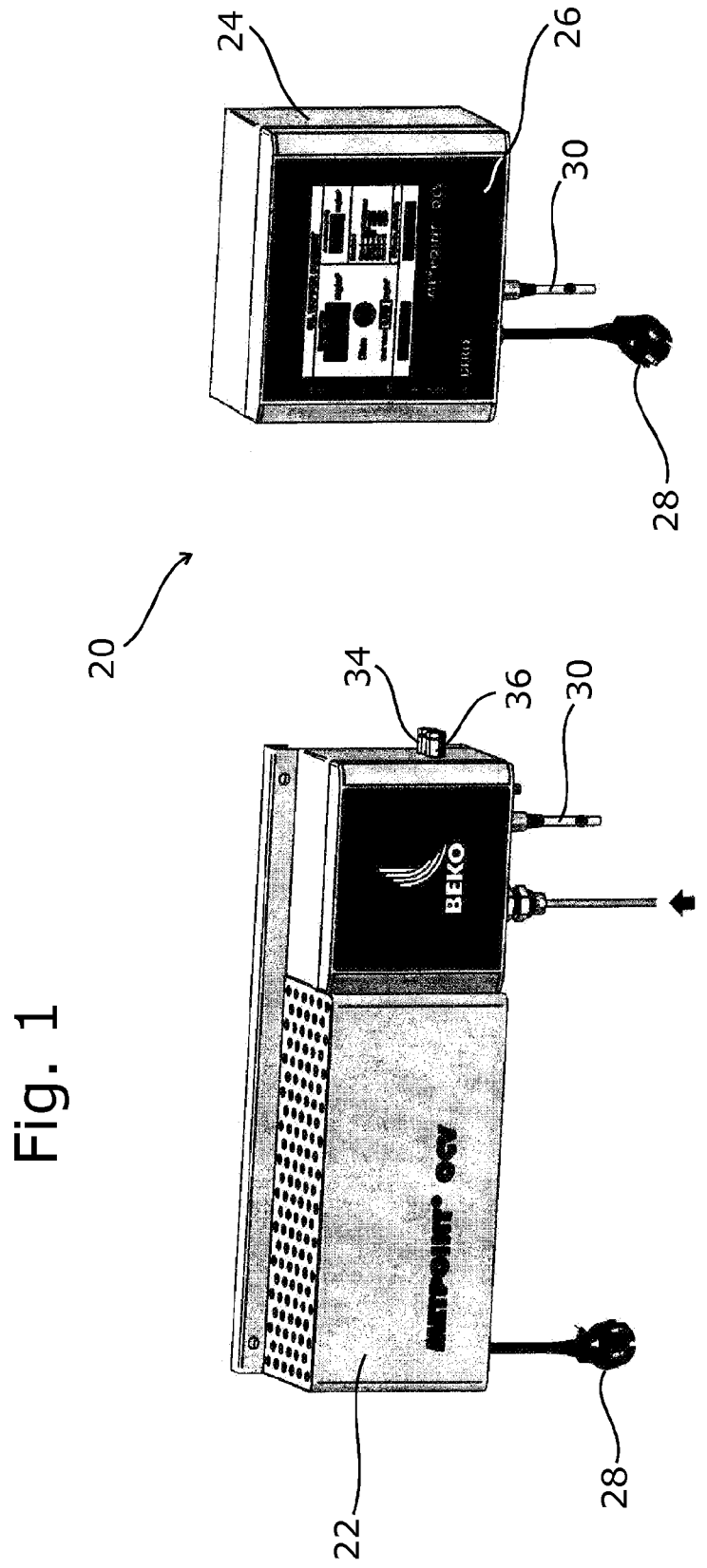
FIG. 1: shows a perspective view of a measuring device according to the invention.

FIG. 1 shows a measuring device 20 according to the invention formed from a sensor unit 22 and an evaluation unit 24. The evaluation unit 24 further comprises a control surface 26, which is configured as a touchscreen. Both devices are equipped with a plug 28 for electrical connection.

Furthermore, both devices comprise signal cable connectors 30 through which they can be connected with each other. Instead of the signal cable connectors 30, however, a wireless radio connection is also advantageously conceivable, which makes installation considerably easier depending on the on-site conditions. It can be seen, moreover, that the sensor unit 22 comprises a measuring gas connector 32 through which the gas to be measured is supplied. Moreover, a zero gas connector 34 for the supply of zero gas and a calibration gas connector 36 for the supply of calibration gas with known ingredients can be seen. The control surface 26 not only serves for controlling the measuring device 20; in the exemplary embodiment shown it also constitutes the display of the measuring device 20. A reference gas unit 38, which cannot be seen (see FIG. 3) and can be configured as an oxidation catalyst, is disposed within the sensor unit 22.

Figure 2:
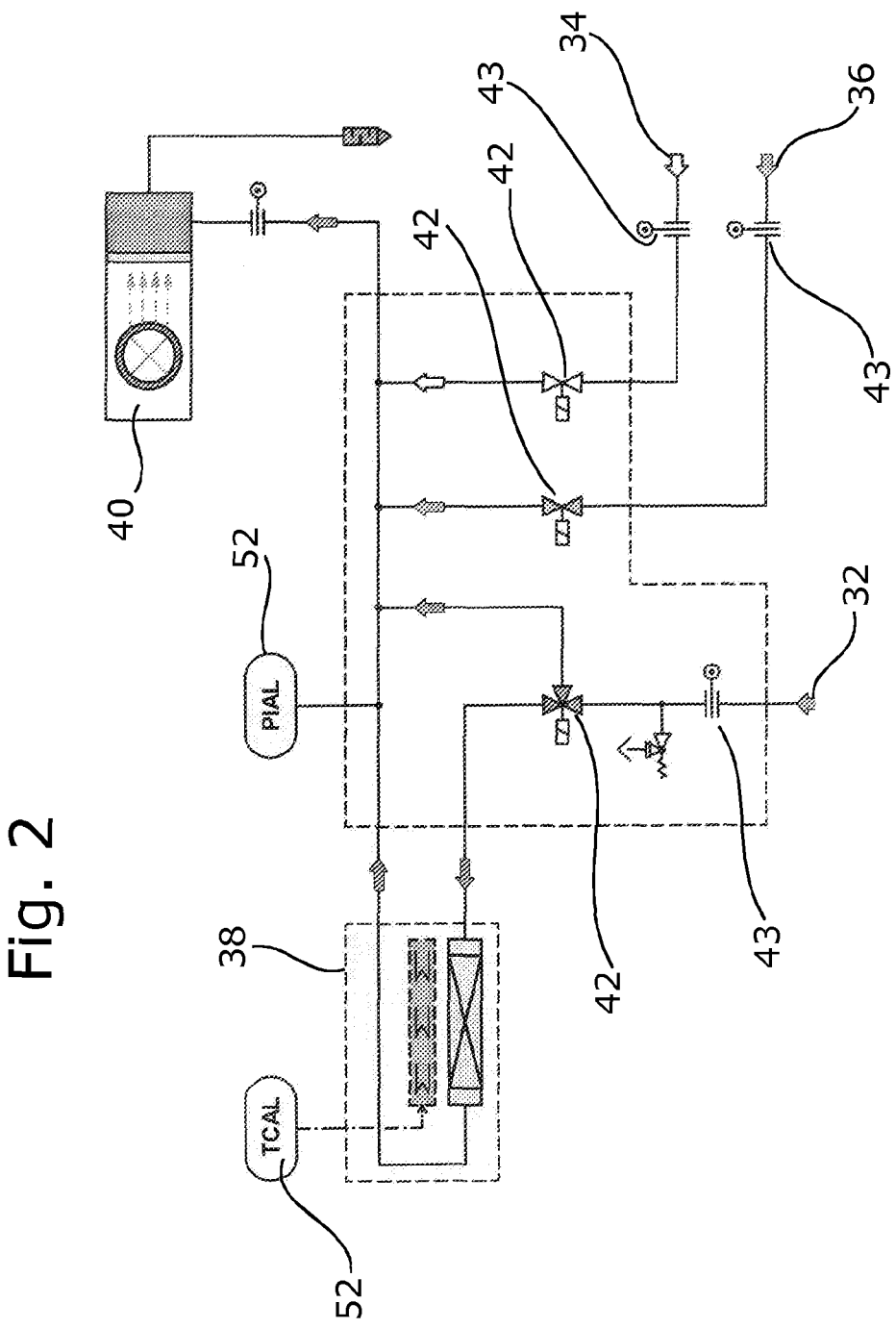
FIG. 2: shows a functional diagram or circuit diagram of the fluid streams of the measuring device.

The function according to the invention of the measuring device becomes clear from FIG. 2. The three gas supplies, namely the measuring gas connector 32, the zero gas connector 34 and the calibration gas connector 36 can be seen. Moreover, the reference gas unit 38 and a sensor 40, which is configured as a photoionization detector, in a measuring chamber 50 are recognizable. The various gas streams are switched or regulated via valves 42. Preferably, the valves 42 are configured as magnetic valves. Accordingly, it is possible to feed the measuring gas to be examined via the measuring gas connector 32 to the reference gas unit and thence, as a reference gas, to the sensor 40. As an alternative, however, it is also possible to feed the measuring gas directly to the sensor 40. It is also possible to feed calibration gas or even zero gas to the sensor 40 together or alternately.

Flow resistors 43 ensure a constant pressure and a constant volumetric flow rate.

Finally, monitoring elements 52 are provided which, for example, raise an alarm if the operating pressure in the measuring device 20 becomes too high.

The evaluation unit 24 can have suitable connectors for a computer or a data base; connectors for data storage devices, such as SD cards, USB sticks and the like can also be provided. The evaluation unit 24 further comprises a data storage device for data storage, and, for calculation and evaluation of the measurement data, a corresponding processor.

The reference gas unit 38 is connected to the valve housing 48 and the measuring chamber 50 through lines 54. Another line 54 leads out from the measuring chamber 50 and ends in an outlet 56. Furthermore, the measuring chamber 50 is connected to the valve housing 48.

Figure 3:
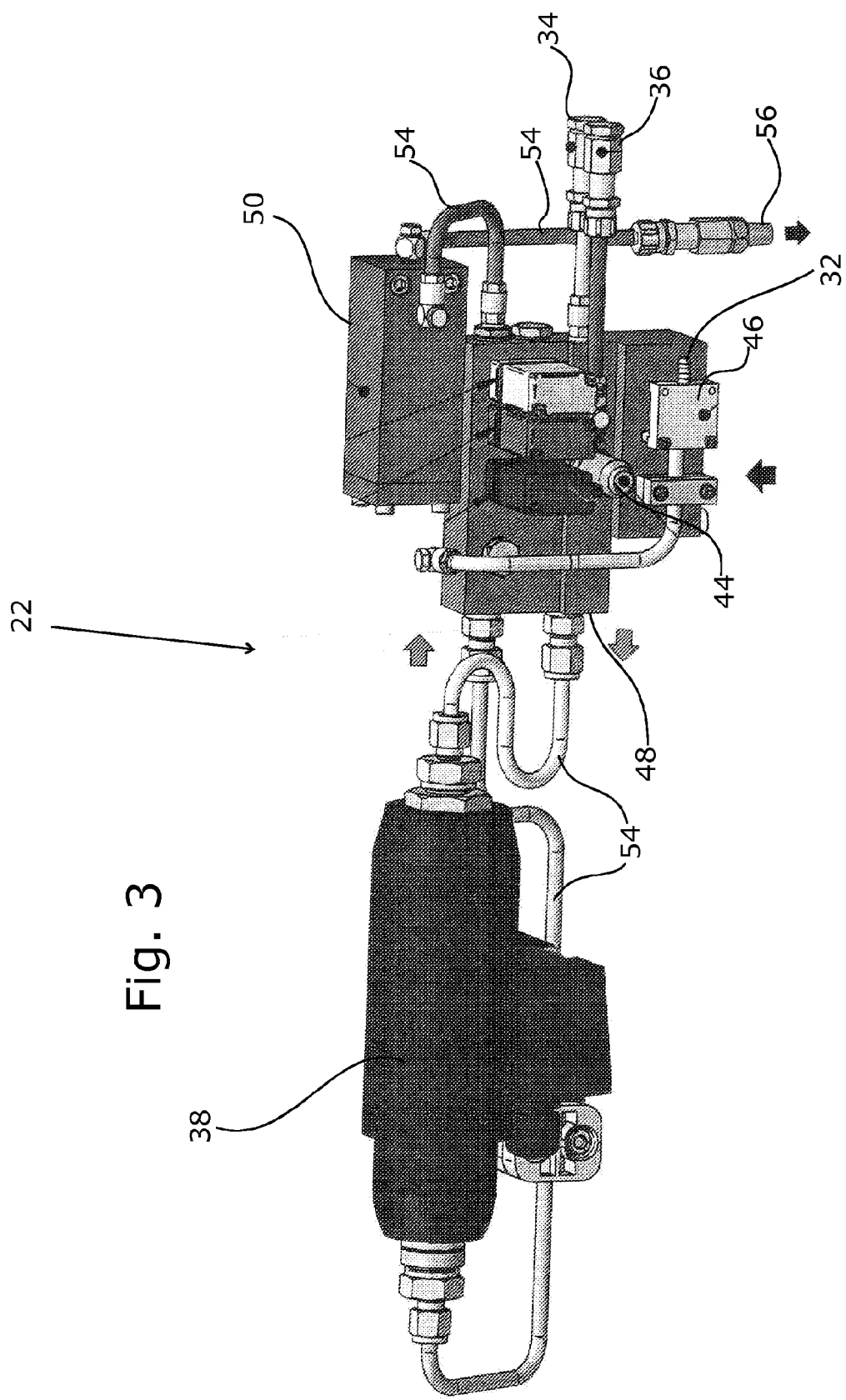
FIG. 3: shows a sensor unit according to the invention without the housing surrounding it.

FIG. 3 illustrates the compact structure of the sensor unit 22 with the integrated reference gas unit 38. In particular, the zero gas connector 34 and the calibration gas connector 36, the reference gas unit 38, the sensor 40 and a safety valve 44 can be seen. A flow monitoring device 46 with a corresponding pressure switch is also provided. The valves 42 and other electric and electronic components are accommodated within a valve housing 48. The sensor 40 is disposed within a measuring chamber 50. The flow resistors 43 (throttles) are integrated into the respective connector screw fittings of the gas connectors 32, 34, 36 and therefore cannot be seen.

What is claimed is:

1. A measuring device for detecting hydrocarbon content in gases of a gas source, wherein the measuring device comprises a reference gas unit and a sensor adapted to detect hydrocarbon content in gases, and the measuring device is further configured to detect the hydrocarbon content in a first gas stream and a second gas stream originating from the same gas source utilizing said sensor, the first gas stream being unchanged and the second gas stream being processed by the reference gas unit before it is fed to said sensor, the first gas stream and the second gas stream being fed to said sensor in an alternating manner, wherein the measuring device is configured to determine the hydrocarbon content in gases from the gas source based on a difference between signals generated by the measuring device upon examining the first gas stream and upon examining the second gas stream, wherein the reference gas unit comprises an oxidation catalyst adapted to oxidize hydrocarbons in the second gas stream, thereby increasing the humidity of the second gas stream, and the measuring device is further configured to admix a dry test gas to the second gas stream before it is fed to said sensor to provide the second gas stream substantially corresponding to the first gas stream in humidity content.

2. The measuring device according to claim 1, wherein the measuring device includes a zero gas connector connectible to a supply of dry gas and a calibration gas connector connectible to a supply of calibration gas with known ingredients for calibrating the measuring device.

3. The measuring device according to claim 1, further comprising flow resistors adapted to provide a constant pressure and a constant volumetric flow rate of the first gas stream and the second gas stream.

4. The measuring device according to claim 1, wherein the measuring device is configured and adapted to autonomously perform calibration processes.

5. The measuring device according to claim 1, wherein the measuring device includes (i) a sensor unit having said sensor, and (ii) an evaluation unit having a display and a control surface.

6. The measuring device according to claim 5, wherein the sensor comprises a photoionization sensor.

7. A method for detecting hydrocarbon content in a gas stream, comprising:
dividing a source gas stream into a first gas stream and a second gas stream; and
examining with a measuring device having a sensor unit comprising a sensor adapted to detect hydrocarbon content in gases both the first and the second gas stream using said sensor of said measuring device configured and adapted to detect the hydrocarbon content therein, wherein the first gas stream is examined unchanged and the second gas stream is processed by a reference gas unit before it is fed to said sensor and examined, and the first gas stream and the second gas stream being fed to said sensor in an alternating manner, wherein the hydrocarbon content is determined using a difference in signals generated by the measuring device upon examining the first gas stream and upon examining the second gas stream, wherein the reference gas unit comprises an oxidation catalyst that oxidizes hydrocarbons in the second gas stream, thereby increasing the humidity of the second gas stream, and the method further comprises admixing a dry test gas to the second gas stream before it is fed to the sensor in an amount providing the second gas stream substantially corresponding to the first gas stream in humidity content.

8. The method according to claim 7, wherein the measuring device is configured to be calibrated by supplying a zero gas and a calibration gas thereto.

9. The method according to claim 7, further comprising calibrating the measuring device by supplying a zero gas and a calibration gas thereto.

* * * * *